United States Patent [19]

Ide et al.

[11] Patent Number: 4,547,520
[45] Date of Patent: Oct. 15, 1985

[54] 5-OXIME DERIVATIVES OF MILBEMYCINS AND VETERINARY AND AGRICULTURAL USE THEREOF

[75] Inventors: Junya Ide; Shigeki Muramatsu; Yasuo Nakada; Noritoshi Kitano, all of Hiromachi, Japan

[73] Assignee: Sankyo Company Limited, Tokyo, Japan

[21] Appl. No.: 555,185

[22] Filed: Nov. 25, 1983

[30] Foreign Application Priority Data

Nov. 25, 1982 [JP] Japan ............................. 57-206462

[51] Int. Cl.$^4$ ................... A61K 31/365; C07D 493/22
[52] U.S. Cl. ...................................... 514/450; 549/264
[58] Field of Search .......................... 549/264; 424/279

[56] References Cited

U.S. PATENT DOCUMENTS

| | | | |
|---|---|---|---|
| 3,950,360 | 4/1976 | Aoki et al. | 549/264 |
| 4,093,629 | 6/1978 | Fisher | 549/264 |
| 4,171,314 | 10/1979 | Chabala et al. | 549/264 |
| 4,423,209 | 12/1983 | Mrozik | 536/7.1 |

FOREIGN PATENT DOCUMENTS

| | | | |
|---|---|---|---|
| 120589 | 8/1982 | Japan | 549/264 |
| 139081 | 8/1982 | Japan | 549/264 |
| 139080 | 8/1982 | Japan | 549/264 |
| 139079 | 8/1982 | Japan | 546/264 |

Primary Examiner—Jane T. Fan

Attorney, Agent, or Firm—Frishauf, Holtz, Goodman & Woodward

[57] ABSTRACT

Oxime derivatives of 5-didehydromilbemycins A$_3$, A$_4$ and D are represented by the formula:

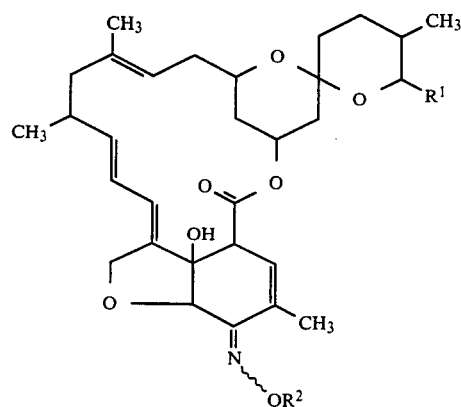

(wherein R$^1$ represents methyl, ethyl or isopropyl, and R$^2$ represents hydrogen, lower alkyl, optionally substituted aralkyl or —CH$_2$COOR$^3$, wherein R$^3$ represents hydrogen or lower alkyl). These and their salts and esters have valuable anthelmintic, acaricidal and insecticidal activity.

40 Claims, No Drawings

5-OXIME DERIVATIVES OF MILBEMYCINS AND VETERINARY AND AGRICULTURAL USE THEREOF

BACKGROUND TO THE INVENTION

The present invention relates to a series of new derivatives of the compounds known as "milbemycins", particularly of milbemycin $A_3$, milbemycin $A_4$ and milbemycin D.

Milbemycin D was disclosed in U.S. Pat. No. 4,346,171, where it was referred to as "compound B-41D", and milbemycins $A_3$ and $A_4$ were disclosed in U.S. Pat. No. 3,950,360. These compounds may be represented by the formula (I):

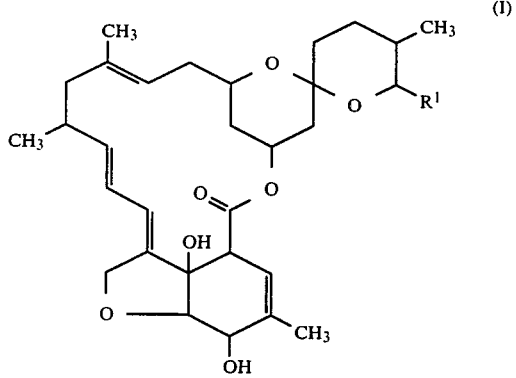

in which $R^1$ represents a methyl group, an ethyl group or an isopropyl group, these compounds being milbemycin $A_3$, milbemycin $A_4$ and milbemycin D, respectively.

These milbemycin compounds may be isolated from cultures of the Streptomyces strain B-41-146, which has been deposited at the Fermentation Research Institute, Agency of Industrial Science and Technology, Ministry of International Trade and Industry, Japan, whence it is available under the accession number FERM-1438. The compounds have been found to have valuable anthelmintic and acaricidal activities.

We have now discovered a series of derivatives of these milbemycins which have demonstrated, in certain tests systems, activities, particularly against ectoparasites, better than the corresponding activities of their parent compounds.

BRIEF SUMMARY OF INVENTION

The compounds of the invention are 5-oxime derivatives of 5-didehydromilbemycins, and may be represented by the formula (II):

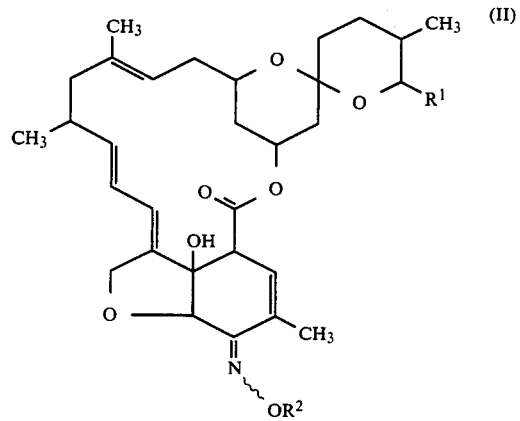

(in which $R^1$ represents a methyl group, an ethyl group or an isopropyl group and $R^2$ represents a hydrogen atom, a $C_1$–$C_6$ alkyl group, an aralkyl group optionally having one or more $C_1$–$C_6$ alkyl, halogen or nitro substituents or a group of formula —$CH_2COOR^3$, in which $R^3$ represents a hydrogen atom or a $C_1$–$C_6$ alkyl group) and, where $R^2$ represents a hydrogen atom, salts and esters thereof.

The invention also provides an anthelmintic, acaricidal and insecticidal composition comprising an anthelmintic, acaricidal and insecticidal compound in admixture with a pharmaceutically, agriculturally or horticulturally acceptable carrier or diluent, wherein the compound is selected from compounds of formula (II), their salts, their esters and mixtures thereof.

The invention still further provides a method of treating an animal, which may be human or non-human, parasitized by a parasite selected from helminths, acarids and insects, which comprises applying to or administering to said animal an active compound, wherein said active compound is selected from compounds of formula (II), their salts, their esters and mixtures thereof.

The invention still further provides a method of protecting animals or plants from damage by parasites selected from the group consisting of acarids, helminths and insects, which comprises applying an active compound to said animals, said plants or to seeds of said plants or to a locus including the same, wherein the active compound is selected from compounds of formula (II), their salts, their esters and mixtures thereof.

DETAILED DESCRIPTION OF INVENTION

In the compounds of formula (II), where $R^2$ or $R^3$ represents a $C_1$–$C_6$ alkyl group, this may be a straight or branched chain group and is preferably a $C_1$–$C_4$ alkyl group, for example a methyl, ethyl, propyl, isopropyl, butyl, isobutyl or sec-butyl group.

Where $R^2$ represents an optionally substituted aralkyl group, it is preferably a benzyl group, which may be unsubstituted or may have one or more $C_1$–$C_6$ alkyl, halogen or nitro substituents. Examples of $C_1$–$C_6$ alkyl groups which may be substituents on the aralkyl group have been given in relation to $R^2$ and $R^3$, and the preferred alkyl group is the methyl group. Preferred halogen atoms which may be substituents on the aralkyl group are the chlorine and bromine atoms. Examples of optionally substituted aralkyl groups thus include the benzyl, m-methylbenzyl, p-methylbenzyl, p-chlorobenzyl, p-bromobenzyl and p-nitrobenzyl groups.

A preferred class of compounds of the present invention are those in which $R^2$ represents a hydrogen atom, a $C_1$-$C_6$ alkyl group, a benzyl group or a carboxymethyl group, most preferably a hydrogen atom.

Compounds in which $R^2$ represents a hydrogen atom can act either as an acid to form salts with a variety of cations, or as a base, to form esters with a variety of acids.

In the case of the salts, the compounds of formula (II) may form salts with a variety of metals, particularly alkali metals (such as lithium, sodium or potassium), alkaline earth metals (such as calcium or barium) or other metals (such as magnesium or aluminium), or with certain organic amines, particularly tertiary amines (such as triethylamine or triethanolamine). Of these, the alkali metal salts and particularly the sodium or potassium salts are preferred.

The esters are preferably with a carboxylic acid, a carbamic acid, a carbonic acid, a sulphonic acid or a phosphoric acid and preferred esters are compounds of formula (IIa):

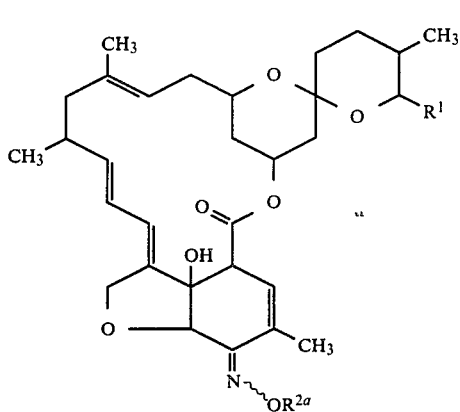

(IIa)

in which $R^1$ is as defined above and $R^{2a}$ represents:

a group of formula —$COR^4$, in which $R^4$ represents a $C_1$-$C_6$ alkyl group, an aralkyl group optionally having one or more $C_1$-$C_6$ alkyl, halogen or nitro substituents, a phenyl group optionally having one or more $C_1$-$C_6$ alkyl, halogen, nitro, carboxy or $C_2$-$C_7$ alkoxycarbonyl substituents or a group of formula —$(CH_2)_nCOOR^5$, wherein n is an integer from 1 to 3 and $R^5$ represents a hydrogen atom or a $C_1$-$C_6$ alkyl group;

a group of formula —$CO.NR^6R^7$, wherein $R^6$ represents a hydrogen atom or a $C_1$-$C_6$ alkyl group and $R^7$ represents a hydrogen atom, a $C_1$-$C_6$ alkyl group, an aryl group or a group of formula —$CH(R^8).COOR^9$ (wherein $R^8$ and $R^9$ are the same or different and each represents a hydrogen atom or a $C_1$-$C_6$ alkyl group);

a group of formula —$COOR^{10}$, wherein $R^{10}$ represents a $C_1$-$C_6$ alkyl group, an aralkyl group optionally having one or more $C_1$-$C_6$ alkyl, halogen or nitro substituents, an aryl group or a group derived by removing an omega-hydroxy group from an optionally protected sugar alcohol;

a group of formula —$SO_2R^{11}$, wherein $R^{11}$ represents a $C_1$-$C_6$ alkyl group or an aryl group; or a group of formula —$(Y^1\!\!=\!\!)P(-\!\!Y^2\!\!-\!\!R^{12})_2$, in which $Y^1$ and $Y^2$, which may be the same or different, each represents an oxygen atom or a sulphur atom and the two atoms represented by $Y^2$ may be the same or different, and each of the groups represented by $R^{12}$, which may be the same or different, is a $C_1$-$C_6$ alkyl group.

Where $R^4$, $R^5$, $R^7$, $R^8$, $R^9$, $R^{10}$ or $R^{12}$ represents a $C_1$-$C_6$ alkyl group, it may be a straight or branched chain group and is preferably a $C_1$-$C_4$ alkyl group, such as a methyl, ethyl, propyl, isopropyl, butyl, isobutyl or sec-butyl group. Where $R^6$ or $R^{11}$ represents a $C_1$-$C_6$ alkyl group, it may be one of these groups but is preferably a methyl or ethyl group.

Where $R^4$ or $R^{10}$ represents an optionally substituted aralkyl group, it may be any of the groups hereinbefore exemplified for $R^2$.

Where $R^4$ represents an optionally substituted phenyl group, the substituents are $C_1$-$C_6$ alkyl, halogen, nitro, carboxy or $C_2$-$C_7$ alkoxycarbonyl substituents. Examples of such groups represented by $R^4$ include the phenyl, o-tolyl, m-tolyl, p-tolyl, o-chlorophenyl, m-chlorophenyl, p-chlorophenyl, o-bromophenyl, m-bromophenyl, p-bromophenyl, p-nitrophenyl, o-carboxyphenyl, m-carboxyphenyl, p-carboxyphenyl, o-methoxycarbonylphenyl, m-methoxycarbonylphenyl, p-methoxycarbonylphenyl, o-ethoxycarbonylphenyl, m-ethoxycarbonylphenyl or p-ethoxycarbonylphenyl groups.

Where $R^7$, $R^{10}$ or $R^{11}$ represents an aryl group, it is preferably a phenyl, tolyl or 2,4,6-trimethylphenyl group.

Where $R^{10}$ represents a group derived by the removal of an omega-hydroxy group from an optionally protected sugar alcohol, the sugar alcohol may be, for example, glycerol, erythritol, threitol, arabinitol, adonitol, xylitol, sorbitol, mannitol or dulcitol. The protecting group or groups on such alcohols may be chosen from a wide variety of such groups and are not critical to the present invention. Examples of such groups include aliphatic acyl groups (such as the formyl or acetyl groups), cyclic ether groups (such as the tetrahydro-2-furanyl or tetrahydro-2-pyranyl groups), 1-alkoxyethyl groups (such as the 1-methoxyethyl or 1-ethoxyethyl groups) or silyl groups (such as the trimethylsilyl, triethylsilyl or dimethyl-t-butylsilyl groups). Alternatively, or in addition, the hydroxy groups at the 1- and 2-positions or the hydroxy groups at the 1- and 3-positions may be an alkylene, cycloalkylene or alkylidene group optionally having an aryl substituent, for example a methylene, ethylene, isopropylidene, benzylidene or cyclohexyline group.

Of the esters represented by formula (IIa), the preferred compounds are those in which $R^{2a}$ represents a $C_2$-$C_7$ alkanoyl group, a $C_2$-$C_7$ alkylcarbamoyl group, a ($C_1$-$C_6$ alkoxy)carbonylmethylcarbamoyl group, a $C_2$-$C_7$ alkoxycarbonyl group, a 2,2-dimethyl-1,3-dioxolan-4-ylmethoxycarbonyl group, a $C_1$-$C_6$ alkanesulphonyl group, an arenesulphonyl group, a di($C_1$-$C_6$ alkoxy)phosphinyl group or a ($C_1$-$C_6$ alkoxy)-($C_1$-$C_6$ alkylthio)phosphinyl group.

Most preferred are compounds of formula (IIa) in which $R^{2a}$ represents a $C_2$-$C_7$ alkanoyl group, a $C_2$-$C_7$ alkylcarbamoyl group, a $C_2$-$C_7$ alkoxycarbonyl group or a 2,2-dimethyl-1,3-dioxolan-4-ylmethoxycarbonyl group.

The compounds of formula (II) and (IIa) can exist in the form of syn and anti isomers with respect to the nitrogen atom of the oxime group and the present invention is not limited to either isomer. The compounds may thus be in the form of the syn isomer, the anti isomer or a mixture thereof.

Of all of the compounds of the invention, the derivatives of milbemycin $A_4$ and D [i.e. compounds of formulae (II) and (IIa) and salts and esters where $R^1$ represents an ethyl or isopropyl group] are preferred.

Compounds of formula (II) may be prepared by reacting a compound of formula (III):

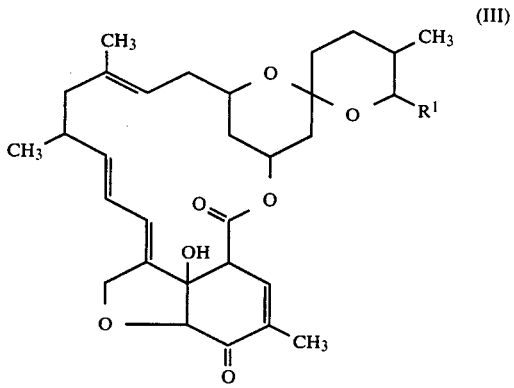

(in which $R^1$ is as defined above) with an oximating agent of formula (IV):

$$NH_2OR^2 \qquad (IV)$$

(in which $R^2$ is as defined above) or a salt thereof in an inert solvent.

The nature of the compound of formula (IV) will, of course, depend upon the particular compound of formula (II) which it is desired to prepare. Suitable salts of this oximating agent of formula (IV) include salts with mineral acids, such as hydrochloric acid, nitric acid or sulphuric acid, the hydrochloride being preferred.

There is no particular limitation on the nature of the solvent employed in this reaction, provided that it has no adverse effect on the reaction. Suitable solvents include: alcohols, such as methanol, ethanol or propanol: ethers, such as diethyl ether, tetrahydrofuran or dioxane; fatty acids, such as acetic acid; mixtures of two or more of these organic solvents; and mixtures of one or more of these organic solvents with water.

The reaction can be carried out over a wide range of temperatures, for example from $-10°$ C. to $+100°$ C., but is preferably carried out at a temperature within the range from $0°$ C. to $50°$ C. At reaction temperatures within these ranges, the reaction will normally require a period of from 30 minutes to 15 hours, preferably from 1 hour to 8 hours.

The reaction can be promoted by carrying it out in the presence of a base, such as sodium acetate, potassium acetate, sodium bicarbonate, sodium carbonate or potassium carbonate.

The compound of formula (III) used as a starting material in this reaction may easily be prepared by oxidising milbemycin $A_3$, milbemycin $A_4$ or milbemycin D, the compounds of formula (I), preferably with chromic anhydride in a conventional manner. These compounds of formula (III) are referred to herein as 5-didehydromilbemycins $A_3$, $A_4$ or D, depending upon whether $R^1$ represents a methyl, ethyl or isopropyl group, respectively. The compounds of the invention are then named as oxime derivatives of the ketone compounds represented by formula (III).

Salts of compounds of formula (II) can readily be prepared by reacting the compound of formula (II) in which $R^2$ represents a hydrogen atom with an appropriate alkali, such as sodium hydroxide, potassium hydroxide, sodium carbonate, potassium carbonate, lithium bicarbonate, sodium bicarbonate or potassium bicarbonate or with one of the aforementioned tertiary amines.

Compounds of formula (IIa) in which $R^{2a}$ represents a residue of a carboxylic acid, an N,N-disubstituted carbamic acid, a carbonic acid, a sulphonic acid or a phosphoric acid can be prepared by reacting a compound of formula (II) in which $R^2$ represents a hydrogen atom with the corresponding acid halide. This reaction is preferably effected in the presence of a base and of an inert solvent. The base serves as an acid-binding agent and any base capable of serving this function without adversely affecting the reagents may be employed. The base is preferably an organic amine, such as triethylamine, N,N-dimethylaniline, pyridine, 4-dimethylaminopyridine, 1,4-diazabicyclo[2.2.2]octane, 5-diazabicyclo[4.3.0]non-5-ene or 1,8-diazabicyclo[5.4.0]undec-7-ene. There is no particular limitation on the nature of the solvent employed in this reaction, provided that it has no adverse effect on the reaction. Suitable solvents include: hydrocarbons, such as hexane, benzene, toluene or xylene; ethers, such as diethyl ether, tetrahydrofuran or dioxane; and halogenated hydrocarbons, such as methylene chloride, chloroform or carbon tetrachloride. The reaction temperature is not particularly critical and, for convenience, we prefer to effect the reaction at about room temperature; at such a temperature, the reaction normally requires a period of from 30 minutes to 5 hours.

Where $R^{10}$ in the group represented by $R^{2a}$ in the compound of formula (IIa) represents a sugar alcohol residue whose hydroxy group or groups are protected, the protecting group may, if desired, be removed by conventional means after this reaction, the precise reaction employed depending upon the nature of the group. For example, where the protecting group is a cyclic ether, silyl, 1-alkoxyethyl, alkylene, cycloalkylene or alkylidene group, this may be removed by treating the product with an acid, such as hydrochloric acid, nitric acid, sulphuric acid, acetic acid, trifluoroacetic acid, methanesulphonic acid or p-toluenesulphonic acid. Where the protecting group is an aliphatic acyl group, it may be removed by reaction with aqueous or alcoholic ammonia. Furthermore, where the protecting group is a silyl group, this can be removed by treatment with tetrabutylammonium fluoride.

Compounds of formula (IIa) in which $R^{2a}$ represents a carbamoyl or N-substituted carbamoyl group may be prepared by reacting a compound of formula (IIa) in which $R^{2a}$ represents a hydrogen atom with an appropriate isocyanate, which may be represented by the general formula (V):

$$R^{13}\text{—NCO} \qquad (V)$$

in which $R^{13}$ represents a monovalent organic group.

This reaction is preferably carried out in the presence of a base and of an inert solvent, examples of which are as exemplified for the reaction between the compound of formula (IIa) and the acid halide. The room temperature is likewise not critical and for convenience the reaction is normally effected at about room temperature; at such a temperature, the reaction normally requires a period of from 1 to 20 hours.

Where the product produced by this reaction is a compound in which $R^{2a}$ represents an N-trihaloacetylcarbamoyl group, this can be converted to the corresponding compound in which $R^{2a}$ represents a carbamoyl group by reacting it with zinc/acetate acid or zinc/methanol as a reducing agent.

After completion of any of the above reactions, the desired product may be recovered from the reaction mixture by conventional means. For example, one suitable recovery technique comprises: pouring the reaction mixture (if necessary after removing insoluble materials) into iced water; if necessary neutralising the mixture with a base or an acid; and then extracting the mixture with a water-immiscible organic solvent. After drying the organic extract and distilling off the solvent, the resulting residue can, if necessary, be further purified by such conventional techniques as recrystallisation and/or column chromatography.

The compounds of the invention have a strong acaricidal activity against, for example, adults, imagos and eggs of Tetranychus, Panonychus and rust mites, which are parasitic to fruit trees, vegetables and flowers. They are also active against Ixodidac, Dermanysside and Sarcoptidae, which are parasitic to animals. Further, they are active against: exoparasites, such as Oestrus, Lucilia, Hypoderma, Gautrophilus, lice and fleas, which are parasitic to animals and birds, particularly livestock and poultry; domestic insects, such as cockroaches and houseflies; and various harmful insects in agricultural and horticultural areas, such as aphids and larval Lepidoptera. They are also effective against Meloidogyne in the soil, Bursaphelenchus and Phizoglyphus. They are also effective against insects of the orders Coleoptera, Homoptera, Heteroptera, Diptera, Thysanoptera, Orthoptera, Anoplura, Siphonaptera, Mallophage, Thysanura, Isoptera, Psocoptera, and Hymenoptera.

The compounds of the invention equally can be used to control other plant-damaging insects, particularly insects that damage plants by eating them. The compounds can be used to protect both ornamental plants and productive plants, particularly cotton (e.g. against *Spodoptera littoralis* and *Heliothis virescens*), as well as vegetable crops (e.g. against *Leptinotarsa decemlineata* and *Myzus perisicae*) and rice crops (e.g. against *Chilo suppressalis* and Laodelphax).

The activity of the compounds of the invention is pronounced, both systemically and by contact. Accordingly, the compounds are very effective against sucking insects, especially sucking insects of the order Homoptera and most particularly the family Aphididae (such as *Aphis fabae, Aphis craccivora* and *Myzus persicae*), which are difficult to control with known compositions.

Accordingly, the compounds of the invention can be used to treat all manner of plants (as well as the seeds from which such plants are grown and the environment containing such plants) to protect them from insects such as those exemplified above. Such plants include cereals (e.g. maize or rice), vegetables (e.g. potatoes or soybeans), fruits and other plants (e.g. cotton).

The compounds of the invention can similarly be used to protect animals from a variety of ectoparasites, by applying the compounds to the animals or to the animals' environment, e.g. livestock housing, animal boxes, abattoirs, pasture land and other grasslands, as well as to any other places lible to be infested. The compounds may also be applied to external parts of the animals, preferably before they are infested.

Moreover, the compounds of the invention are effective against various parasitical helminths. These parasites can attack livestock, poultry and pet animals (such as pigs, shejep, goats, cows, horses, dogs, cats anf fowl) and can cause grave economic damage. Among the helminths, the nematodes in particular often cause serious infection. Typical genera of nematodes which are parasitic on these animals and against which the compounds of the invention are effective include:

Haemonchus,
Trichostrongylus,
Ostertagia,
Nematodirus,
Cooperia,
Ascaris,
Bunostomum,
Oesophagostomum,
Chabertia,
Trichuris,
Strongylus,
Trichonema,
Dictyocaulus,
Capillaria,
Heterakis,
Toxocara,
Ascaridia,
Oxyuris,
Ancylostoma,
Uncinaria,
Toxascaris and
Parascaris.

Certain parasitical species of the genera Nematodirus, Cooperia and Oesophagostomum attack the intestines, while certain species of the genera Haemonchus and Ostertagia parasitize the stomach, and parasites belonging to the genus Dictyocaulus are found in the lungs. Parasites belonging to the families Filariidae and Setariidae are found in internal tissues and organs, for example, the heart, the blood vessels, the subcutaneous tissues and the lymphatic vessels. The compounds of the invention are active against all these parasites.

The compounds of the invention are also effective against parasites which infect humans. Typical of the parasites which may most commonly be found in the digestive tracts of human beings are parasites of the genera Ancylostoma, Necator, Ascaris, Strongyloides, Trichinella, Capillaria, Trichuris and Enterobius. The compounds are also active against parasites of the genera Wuchereria, Brugia, Onchocerca and Loa of the family Filariidae (which are found in blood, tissues and organs other than the digestive tract and are medically important), parasites of the genus Dracanculus and parasites of the genera Strongyloides and Trichinella, which especially infect the exointestinal canal.

The form of the compositions of the invention and the nature of the carriers or diluents employed in them will vary depending upon the intended use of the composition. For example, where the compounds of the invention are to be employed as anthelmintics, they are preferably administered orally, parenterally or topically and the form of compositions chosen will be appropriate to the intended route of administration.

For oral administration, the composition of the invention is preferably in the form of a liquid drink comprising a non-toxic solution or suspension, preferably aqueous, of the active compound in admixture with a suspending agent (such as bentonite), a wetting agent or other diluents. The drink, in general, also contains an anti-foaming agent. The active compound would normally be present in the drink in an amount of from 0.01 to 0.5% by weight, more preferably from 0.01 to 0.1% by weight.

Compositions for oral administration may also be in the form of dry solids, preferably in unit dosage form, such as capsules, pills or tablets containing the desired amount of the active compound. These compositions may be prepared by mixing the active compound uniformly with suitable diluents, fillers, disintegrators and/or binding agents, for example starch, lactose, talc, magnesium stearate and vegetable gum. The weight and contents of the preparation will vary widely, depending upon the nature of the animal to be treated, the degree of infection, the nature of the parasite and the body weight of the animal to be treated.

The compounds may also be administered as an additive to animal feedstuffs, in which case they may be dispersed uniformly in the feedstuffs, used as a top dressing or used in the form of pellets. The content of active compound in the feedstuff is preferably from 0.0001 to 0.02%, in order to achieve the desired anthelmintic activity.

For parenteral administration, the compound of the invention is preferably dissolved or suspended in a liquid vehicle, preferably a vegetable oil, such as peanut oil or cottonseed oil. Where the compound is a salt of a compound of formula (II), the liquid vehicle may be water or another aqueous medium. Depending upon the animal to be treated, the injection may be subcutaneous or into the proventriculus, a muscle or the trachea. Such preparations would normally contain the active compound at a concentration of from 0.05 to 50% by weight.

The compounds of the invention may also be administered topically in admixture with a suitable carrier, such as dimethyl sulphoxide or a hydrocarbon solvent. Such preparations would be applied directly to the outside of the animal by spraying (e.g. by a hand spray or in spray races), by dipping (e.g. in a plunge dip), by a pour-on solution or by manual methods (e.g. hand-dressing).

The dose of active compound may be varied, depending upon the nature of the animal to be treated, and the nature and degree of parasitic infection. However, best results for oral administration are achieved when the dose is from 0.01 to 100 mg, more preferably from 0.5 to 50 mg, per 1 kg body weight. The compound may be administered in a single dose or in divided doses for a relatively short period, such as from 1 to 5 days.

Where the composition of the invention is intended for agricultural or horticultural use, a variety of forms and formulations are possible. For example, it may be formulated as dusts, coarse dusts, soluble powders, microgranules, fine microgranules, wettable powders, dilute emulsions, emulsifiable concentrates, aqueous or oily suspensions or solutions (which may be directly sprayable or for dilution), aerosols or capsules in, for example, polymeric substances. The carrier employed may be natural or synthetic and organic or inorganic; it is generally employed to assist the active compound to reach the substrate to be treated, and to make it easier to store, transport or handle the active compound. Solid, liquid and gaseous carriers may be employed, chosen from carriers well known in the art for use with compositions of this type.

Such formulations may be prepared by conventional means, e.g. by intimate mixing and/or grinding of the active ingredient(s) with the carrier or diluent, e.g. solvent, solid carrier or, optionally, surface-active agent.

Suitable solvents include: aromatic hydrocarbons, preferably the $C_8$ to $C_{12}$ fractions from petroleum distillation, such as xylene mixtures or substituted naphthalenes; esters of phthalic acid, such as dibutyl or dioctyl phthalate; aliphatic hydrocarbons, such as cyclohexane or the paraffins; alcohols and glycols or esters thereof, such as ethanol, ethylene glycol, ethylene glycol monomethyl ether or ethylene glycol monoethyl ether; ketones, such as cyclohexanone; strongly polar solvents, such as N-methyl-2-pyrrolidone, dimethyl sulphoxide or N,N-dimethylformamide; optionally epoxidized vegetable oils, such as epoxidized coconut oil or soybean oil; and water.

Solid carriers, which may be used, for example, in dusts and dispersible powders, include natural mineral fillers, such as calcite, talc, kaolin, montmorillonite or attapulgite. In order to improve the physical properties of the composition, it is also possible to add highly dispersed silicic acid or highly dispersed absorbent polymers. Suitable granulated adsorptive carriers may be porous (such as pumice, ground brick, sepiolite or bentonite) or non-porous (such as calcite or sand). A wide variety of pregranulated materials, organic or inorganic, may also be used; examples include dolomite and ground plant residues.

Surface-active agents which may be used are well known in the art and may be non-ionic, cationic or anionic agents having good emulsifying, dispersing and wetting properties. Mixtures of such agents may also be used.

Compositions may also contain stabilizers, anti-foaming agents, viscosity regulators, binders or adhesives or any combination thereof, as well as fertilizers or other active substances to achieve special effects.

Pesticidal compositions will generally contain: from 0.01 to 99%, more preferably from 0.1 to 95%, by weight of the active compound; from 1 to 99.99% of a solid or liquid additive; and from 0 to 25%, more preferably from 0.1 to 25%, of a surface-active agent. Whereas commercial products are generally sold as concentrated compositions, they are generally diluted by the end-user to a concentration of from 0.001 to 0.0001% by weight (from 10 to 1 ppm).

The invention is further illustrated by the following Examples, of which Examples 1 to 15 illustrate the preparation of various compounds of the invention, Examples 16 to 20 demonstrate the activity of compounds of the invention and the preparation of a starting material for the Examples is illustrated in the Preparation.

PREPARATION

5-Didehydromilbemycin D

A solution of 2.78 g of milbemycin D in 50 ml of methylene chloride were added dropwise, with ice-cooling, to a chromic anhydride/pyridine complex prepared from 5.0 g of chromic anhydride, 8.0 g of pyridine and 115 ml of methylene chloride. The mixture was then stirred with ice-cooling for 1 hour after which it was mixed with 700 ml of hexane and filtered using a Celite (trade mark) filter aid. The filtrate was concentrated by evaporation under reduced pressure and the residue was subjected to column chromatography through 100 g of silica gel eluted with a 90:10 by volume mixture of hexane and ethyl acetate, to give 1.5 g of the title compound.

Infrared Absorption Spectrum (Nujol-trade markmull) $\nu_{max}$ cm$^{-1}$: 3470, 1735, 1680.

Nuclear Magnetic Resonance Spectrum (CDCl$_3$) $\delta$ ppm: 6.50 (1H, singlet, —CH= at 3-position); 3.80 (1H, singlet, CH at 6-position); 4.71 (2H, multiplet, CH$_2$ at 26-position).

Mass Spectrum (m/e): 554(M+).

EXAMPLE 1

5-Didehydromilbemycin D 5-oxime 62.5 mg of hydroxylamine hydrochloride were added at 10°–15° C. to a mixture of 5 ml of dioxane, 54 mg of acetic acid and 74 mg of sodium acetate, after which the mixture was stirred at the same temperature for 5 minutes. 166 mg of 5-didehydromilbemycin D (prepared as described in the Preparation) were then added to the mixture, which was stirred at room temperature for 1 hour. A further 74 mg of sodium acetate and 62.5 mg of hydroxylamine hydrochloride were added to the mixture, which was then stirred at room temperature for 40 minutes. 5 drops of water were added to the mixture and it was then stirred at room temperature for 2.5 hours, after which it was concentrated by evaporation under reduced pressure to one half of its original volume. This concentrate was diluted with water and extracted with diethyl ether. The extract was dried over anhydrous sodium sulphate and the solvent was distilled off under reduced pressure. The resulting residue was isolated and purified by column chromatography through silica gel eluted with a 3:2 by volume mixture of hexane and ethyl acetate, to give 76 mg of the title compound. In addition, 53 mg of 3-hydroxyamino-5-didehydro-3,4-dihydromilbemycin D 5-oxime were obtained.

Infrared Absorption Spectrum (Nujol mull) $\nu_{max}$ cm$^{-1}$: 3350, 1715.

Nuclear Magnetic Resonance Spectrum (CDCl$_3$) $\delta$ ppm: 1.91 (3H, singlet, CH$_3$ at 4-position); 3.95 (1H, singlet, OH at 7-position); 4.63 (1H, singlet, CH at 6-position); 4.68 (2H, multiplet, CH$_2$ at 26-position); 8.20 (1H, singlet, =N—OH).

Mass Spectrum (m/e): 569(M+), 551 (M-18).

EXAMPLE 2

5-Didehydromilbemycin D 5-oxime

A solution of 166 mg of 5-didehydromilbemycin D in 2 ml of methanol and 2 ml of dioxane was added dropwise to a solution of 125 mg of hydroxylamine hydrochloride in water, and then the mixture was stirred for 6 hours at room temperature. The solvent was removed from the mixture by evaporation under reduced pressure, after which diethyl ether was added to the residue and the ethereal solution was washed with water and then dried over anhydrous sodium sulphate. The solvent was distilled off under reduced pressure and the resulting residue was purified by column chromatography through silica gel eluted with a 3:1 by volume mixture of hexane and acetone, to give 145 mg of the title compound, whose properties were the same as the properties of the product of Example 1.

EXAMPLE 3

5-Didehydromilbemycin A$_4$ 5-oxime

The procedure described in Example 2 was repeated, to give 770 mg of the title compound, melting at 175°–185° C., from 820 mg of 5-didehydromilbemycin A$_4$ and 630 mg of hydroxylamine hydrochloride.

Infrared Absorption Spectrum (Nujol mull) $\nu_{max}$ cm$^{-1}$: 3340, 1710.

Mass Spectrum (m/e): 555(M+), 537 (M-18).

EXAMPLE 4

5-Didehydromilbemycin D 5-O-methyloxime

Following the procedure described in Example 2, 97 mg of the title compound, melting at 141°–160° C., were obtained from 109 mg of 5-didehydromilbemycin D and 100 mg of methoxyamine hydrochloride.

Infrared Absorption Spectrum (CCl$_4$) $\nu_{max}$ cm$^{-1}$: 3500, 1715.

Mass Spectrum (m/e): 583(M+), 565 (M-18).

EXAMPLE 5

5-Didehydromilbemycin D 5-O-benzyloxime

Following the procedure described in Example 2, 420 mg of the title compound, melting at 115°–120° C., were obtained from 510 mg of 5-didehydromilbemycin D and 880 mg of benzyloxyamine hydrochloride.

Infrared Absorption Spectrum (Nujol mull) $\nu_{max}$ cm$^{-1}$: 3480, 1715.

Mass Specktrum (m/e): 659(M+), 641 (M-18).

EXAMPLE 6

5-Didehydromilbemycin D 5-O-(carboxymethyl)oxime

Following the procedure described in Example 2, 370 mg of the title compound, melting at 135°–143° C., were obtained from 350 mg of 5-didehydromilbemycin D and 470 mg of carboxymethoxyamine hemihydrochloride.

Infrared Absorption Spectrum (Nujol mull) $\nu_{max}$ cm$^{-1}$: 3550, 1735.

Mass Spectrum (m/e): 627(M+), 609 (M-18).

EXAMPLE 7

5-Didehydromilbemycin D 5-O-(ethoxycarbonyl)oxime 100 mg of triethylamine, followed by 80 mg of ethyl chloroformate, were added at 0° C. to a solution of 410 mg of 5-didehydromilbemycin D 5-oxime in 8 ml of methylene chloride. The mixture was stirred for 1 hour at room temperature and then poured into iced-water, after which it was extracted three times with diethyl ether. The combined extracts were washed successively with 0.1N hydrochloric acid, with water and with a saturated aqueous solution of sodium chloride, after which they were dried over anhydrous magnesium sulphate. The solvent was removed by evaporation under reduced pressure, and then the residue was purified by column chromatography through silica gel eluted with a 3:1 by volume mixture of hexane and ethyl acetate, to afford 276.3 mg (yield 60%) of the title compound as a glass melting at 134°–140° C.

Infrared Absorption Spectrum (CCl$_4$) $\nu_{max}$ cm$^{-1}$: 3480, 1785, 1715.

Mass Spectrum (m/e): 641(M+), 623 (M-18).

EXAMPLE 8

5-Didehydromilbemycin D 5-O-(methylcarbonyl)oxime

Following the procedure described in Example 7, 300 mg of the title compound, melting at 147°–152° C., were obtained from 400 mg of 5-didehydromilbemycin D 5-oxime and 0.055 ml of acetyl chloride.

Infrared Absorption Spectrum (Nujol mull) $\nu_{max}$ cm$^{-1}$: 3460, 1780, 1735, 1710.

Mass Spectrum (m/e): 611(M+), 593 (M-18), 568 (M-43).

EXAMPLE 9

5-Didehydromilbemycin D 5-O-(2,2-dimethyl-1,3-dioxolan-4-ylmethoxycarbonyl)oxime Following the procedure described in Example 7, 610 mg of the title compound, melting at 115°–119° C., were obtained from 600 mg of 5-didehydromilbemycin D 5-oxime and 0.6 ml of 2,2-dimethyl-1,3-dioxolan-4-ylmethyl chloroformate.

Mass Spectrum (m/e): 727(M+), 569 (M-158).

EXAMPLE 10

5-Didehydromilbemycin D 5-O-mesyloxime

Following the procedure described in Example 7, 400 mg of the title compound, melting at 147°–150° C. (with decomposition), were obtained from 400 mg of 5-didehydromilbemycin D 5-oxime and 0.1 ml of methanesulphonyl chloride.

Mass Spectrum (m/e): 647(M+).

EXAMPLE 11

5-Didehydromilbemycin D 5-O-p-tosyloxime

Following the procedure described in Example 7, 420 mg of the title compound, melting at 128°–132° C., were obtained from 470 mg of 5-didehydromilbemycin D 5-oxime and 190 mg of p-tosyl chloride.

Mass Spectrum (m/e): 569(M-154), 551 (M-172), 534 (M-189).

EXAMPLE 12

5-Didehydromilbemycin D 5-O-(O-ethyl-S-propylthiophosphono)oxime

Following the procedure described in Example 7, 230 mg of the title compound, melting at 104°–106° C., were prepared from 330 mg of 5-didehydromilbemycin D 5-oxime and 0.15 ml of O-ethyl S-propyl chlorothiophosphate.

Mass Spectrum (m/e): 569(M-166).

EXAMPLE 13

5-Didehydromilbemycin D 5-O-(2,4,6-trimethylbenzenesulphonyl)oxime

Following the procedure described in Example 7, 390 mg of the title compound, melting at 165°–168° C., were obtained from 450 mg of 5-didehydromilbemycin D 5-oxime and 220 mg of 2,4,6-trimethylbenzenesulphonyl chloride.

EXAMPLE 14

5-Didehydromilbemycin D 5-O-methylcarbamoyloxime 0.20 ml of triethylamine and 0.1 ml of methyl isocyanate were added at room temperature to a solution of 362.6 mg of 5-didehydromilbemycin D 5-oxime in 12.0 ml of methylene chloride. The mixture was stirred for 10 hours at room temperature, after which it was poured into water and extracted three times with diethyl ether. The ethereal extracts were combined and washed successively with 0.1N hydrochloric acid, with water and with a saturated aqueous solution of sodium chloride, after which they were dried over anhydrous magnesium sulphate. The solvent was removed by evaporation under reduced pressure, after which the residue was purified by column chromatography through silica gel, eluted with a 3:1 by volume mixture of hexane and ethyl acetate, to afford 327.1 mg of the title compound as a glass melting at 171°–175° C.

Mass Spectrum (m/e): 626(M+), 608 (M-18), 569 (M-57).

EXAMPLE 15

5-Didehydromilbemycin D 5-O-(methoxycarbonylmethylcarbamoyl)oxime

Following the procedure described in Example 14, 260 mg of the title compound, melting at 112°–115° C., were prepared from 360 mg of 5-didehydromilbemycin D 5-oxime and 0.3 ml of methoxycarbonylmethyl isocyanate.

Mass Spectrum (m/e): 684(M+), 569 (M-115).

EXAMPLE 16

Anthelmintic activity against *Derafilaria immitis*

Dogs having a body weight of 8 to 17 kg, naturally infected by *Derafilaria immitis*, were used as the test animals.

1.0 g of each of the test compounds listed in Tables 1 and 2 were blended with 0.1 g of butylated hydroxytoluene, 10 ml of dimethylacetamide and sufficient polyethylene glycol (PEG-400) to bring the total volume to 100 ml.

Each dog was then given orally or by subcutaneous injection sufficient of this composition to provide either 0.1 mg or 0.05 mg of the test compound per kilogram body weight.

A sample of blood was drawn from the dog's saphena immediately prior to administration of the composition and then one week and two weeks after administration. Using a Zahli pipette, 0.02 ml of the blood sample was smeared thickly onto a glass slide, and then the blood was stained with Giemsa solution and the number of microfilaria was counted microscopically and determined as an average over four glass slides.

The results are reported in Tables 1 and 2 as the percentage reduction of microfilaria from the value before administration of the composition to that achieved 1 or 2 weeks after administration.

TABLE 1

| | Oral Administration | | |
| --- | --- | --- | --- |
| Compd. of Ex. | Amount (mg/kg) | % Reduction of Microfilaria | |
| | | After a week | After two weeks |
| 1 | 0.05 | 95.0 | 95.5 |
| 3 | 0.05 | 93.2 | 93.2 |
| 7 | 0.1 | 98.8 | 98.0 |
| 8 | 0.05 | 63.9 | 79.9 |
| 13 | 0.1 | 61.5 | 81.6 |

TABLE 2

| | Subcutaneous Injection | | |
| --- | --- | --- | --- |
| Compd. of Ex. | Amount (mg/kg) | % Reduction of Microfilaria | |
| | | After a week | After two weeks |
| 1 | 0.05 | 56.0 | 72.2 |
| 3 | 0.05 | 99.9 | 99.7 |

EXAMPLE 17

Acaricidal effect against Boophilus microplus

Engorged female ticks of the species *Boophilus microplus* were fixed dorsally using double-sided adhesive tape on polyvinyl chloride panels in rows, each row containing 10 ticks. Each compound of Examples 1, 3, 4, 7 and 8 was tested as follows:

One series of ticks was treated topically, on their ventral side, and another was treated by injection with doses of from 5 to 0.0005 μg of the test compound, dissolved in 2 or 1 μl of solvent, per tick. The efficacy of the compound for both forms of treatment was evaluated by determining the IR$_{90}$ value, i.e. the dose preventing reproduction in 90% of the female ticks, 30 days after treatment. On the basis of the IR$_{90}$ values, all of the compounds tested were effective in doses of from 0.5 to 5 μg per tick topically and in doses of from 0.005 to 0.05 μg per tick by injection.

EXAMPLE 18

Effectiveness against Aedes aegypti

The compound tested in this Example is that of Example 7.

A dilution series of active ingredient concentrations ranging from 1.0 to 0.1 ppm was obtained by pipetting a specific amount of a 0.01% acetone solution of the compound under test onto the surface of 150 ml of water in a beaker. After the acetone had evaporated, 30-40 2 day old larvae of *Aedes aegypti* were put into each beaker and mortality counts were made after 1, 2 and 5 days.

The compound of Example 7 effected a 80% kill at a concentration of 0.8 ppm.

EXAMPLE 19

Acaricidal activity against Tetranychus urticae and Tetranychus cinnabarius

The primary leaves of plants of the species *Phaseolus vulgaris* were infested with a piece of leaf from a mass culture of *Tetranychus urticae* (organic phosphate-sensitive) or of *Tetranychus cinnabarius* (organic phosphate-tolerant), tolerance being with respect to Diazinon. 16 hours after infection, the infested plants were sprayed, until dripping wet, with a test solution containing the compound under test at a concentration within the range from 0.2 to 1.5 ppm. The plants were assessed after 24 hours and again after 7 days by examining imagos and larvae (all mobile stages) under a binocular microscope, to determine living and dead individuals. One plant was used for each concentration and each test compound. The plants were kept during the test in greenhouse compartments at 25° C. Each of the compounds of Examples 1, 7 and 8 achieved 80% mortality within the test period against acarids of the species *Tetranychus urticae* and *Tetranychus cinnabarius* at concentrations within the range tested.

EXAMPLE 20

Insecticidal activity against Aphis craccivora

Pea seedlings which were well infested with a population of cow pea aphids (*Aphis craccivora*) were treated in a test series in an automatic spray cabin with 40 ml of a test solution containing the compound under test at a concentration within the range from 25 to 1 ppm. The plants bearing the parasites were kept in an air-conditioned greenhouse cabin at 20° C. and 60% relative humidity for 14 hours, under exposure to light, both natural and artificial.

The results of the test were assessed after 3 days by counting the number of living individuals. Treatment with 3 ppm of the compound of Example 7 produced 80% mortality of the aphid population.

We claim:

1. A compound of the formula (II):

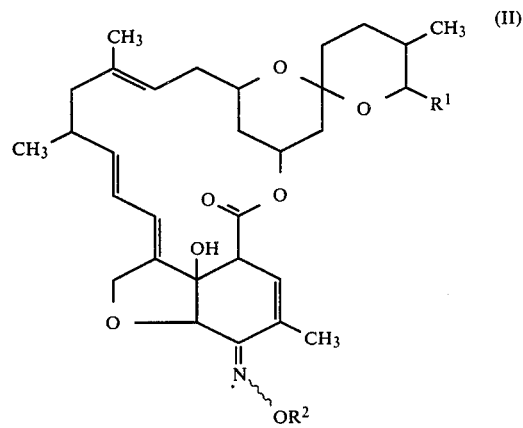

in which $R^1$ represents methyl, ethyl or isopropyl and $R^2$ represents hydrogen, a $C_1$-$C_6$ alkyl group, benzyl, benzyl substituted with one $C_1$-$C_6$ alkyl, halogen or nitro or a group of formula —$CH_2COOR^3$, in which $R^3$ represents hydrogen or a $C_1$-$C_6$ alkyl group; and, when $R^2$ represents hydrogen, a veterinary or an agriculturally acceptable salt or ester thereof.

2. The compound as claimed in claim 1, wherein $R^2$ represents hydrogen, a $C_1$-$C_6$ alkyl group, benzyl or carboxymethyl.

3. The compound as claimed in claim 1, wherein $R^2$ represents a hydrogen atom and said salts and esters thereof.

4. The compound as claimed in claim 2 or claim 3, wherein $R^1$ represents an ethyl or isopropyl group.

5. A compound of formula (IIa):

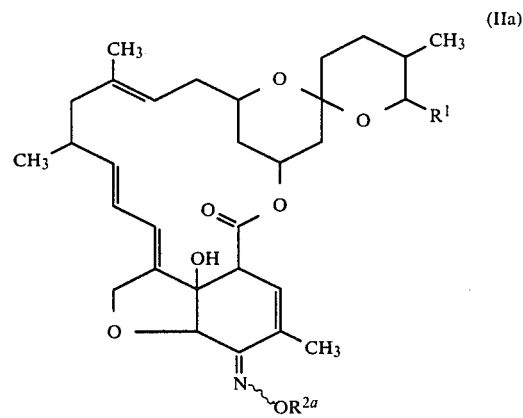

wherein:

$R^1$ represents methyl, ethyl or isopropyl; and $R^{2a}$ represents:

a group of formula —$COR^4$, in which $R^4$ represents a $C_1$-$C_6$ alkyl group, benzyl, benzyl substituted with one $C_1$-$C_6$ alkyl, halogen or nitro, phenyl, phenyl substituted with at least one $C_1$-$C_6$ alkyl, halogen, nitro, carboxy or $C_2$–$C_7$ alkoxycarbonyl substituents or a group of formula —$(CH_2)_n COOR^5$, wherein n is an integer from 1 to 3 and $R^5$ represnts a hydrogen atom or a $C_1$–$C_6$ alkyl group;

a group of formula —$CO.NR^6R^7$, wherein $R^6$ represents hydrogen or a $C_1$–$C_6$ alkyl group and $R^7$ represents hydrogen, a $C_1$–$C_6$ alkyl group, a phenyl group or a group of formula —$CH(R^8).COOR^9$ (wherein $R^8$ and $R^9$ are the same or different and each represents hydrogen at a $C_1$–$C_6$ alkyl group);

a group of formula —$COOR^{10}$, wherein $R^{10}$ represents a $C_1$–$C_6$ alkyl group, benzyl, benzyl substituted with one $C_1$–$C_6$ alkyl, halogen or nitro, a phenyl group or a sugar alcohol from which an omega-hydroxy group has been removed, said sugar alcohol is selected from the group consisting of glycerol, erythritol, threitol, arabinitol, adonitol, xylitol, sorbitol, mannitol and dulcitol; said sugar alcohol may be substituted with at least one protecting group selected from the group consisting of formyl, acetyl, tetrahydro-2-furanyl, tetrahydro-2-pyranyl groups, 1-methoxyethyl, 1-ethoxyethyl, trimethylsilyl, triethylsilyl and dimethyl-t-butylsilyl, and the paired hydroxy groups at the 1- and 2-positions or at the 1- and 3-positions may be joined by replacing the terminal hydrogens of respective paired hydroxy groups with a bridging methylene, ethylene, isopropylidene, benzylidene or cyclohexyline group;

a group of formula —$SO_2R^{11}$, wherein $R^{11}$ represents a $C_1$–$C_6$ alkyl group or a phenyl group; or a group of formula —$(Y^1=)P(-Y^2-R^{12})_2$, in which $Y^1$ and $Y^2$, which may be the same or different, each represents oxygen or sulphur and the two atoms represented by $Y^2$ may be the same or different, and each of the groups represented by $R^{12}$, which may be the same or different, is a $C_1$–$C_6$ alkyl group.

6. The compound as claimed in claim 5, wherein $R^{2a}$ represents a $C_2$–$C_7$ alkanoyl group, a $C_2$–$C_7$ alkylcarbamoyl group, a ($C_1$–$C_6$ alkoxy)carbonylmethylcarbamoyl group, a $C_2$–$C_7$ alkoxycarbonyl group, a 2,2-dimethyl-1,3-dioxolan-4-ylmethoxycarbonyl group, a $C_1$–$C_6$ alkanesulphonyl group, a benzenesulphonyl group, a di($C_1$–$C_6$ alkoxy)phosphinyl group or a ($C_1$–$C_6$ alkoxy)-($C_1$–$C_6$ alkylthio)phosphinyl group.

7. The compound as claimed in claim 5, wherein $R^{2a}$ represents a $C_2$–$C_7$ alkanoyl group, a $C_2$–$C_7$ alkylcarbamoyl group, a $C_2$–$C_7$ alkoxycarbonyl group or a 2,2-dimethyl-1,3-dioxolan-4-ylmethoxycarbonyl group.

8. The compound as claimed in claim 6 or claim 7, wherein $R^1$ represents an ethyl or isopropyl group.

9. The compound as claimed in any one of claims 1, 2 and 3, wherein the salt is selected from sodium and potassium salts.

10. The compound as claimed in claim 9, wherein $R^1$ represents ethyl or isopropyl.

11. An anthelmintic, acaricidal and insecticidal composition comprising an effective amount of an anthelmintic, acaricidal and insecticidal compound in admixture with a pharmaceutically, agriculturally or horticulturally acceptable carrier or diluent, wherein said compound is selected from compounds of formula (II):

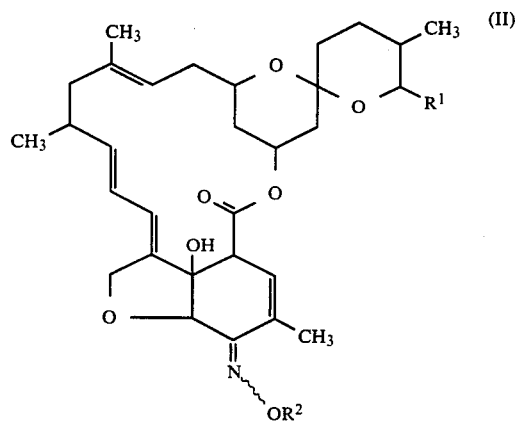

in which $R^1$ represents methyl, ethyl or isopropyl and $R^2$ represents hydrogen, a $C_1$–$C_6$ alkyl group, benzyl, benzyl substituted with one $C_1$–$C_6$ alkyl, halogen or nitro or a group of formula —$CH_2COOR^3$, in which $R^3$ represents hydrogen or a $C_1$–$C_6$ alkyl group; and, when $R^2$ represents hydrogen, pharmaceutically, agriculturally or horticulturally acceptable salt or ester thereof.

12. A composition as claimed in claim 11, wherein $R^2$ represents hydrogen, a $C_1$–$C_6$ alkyl group, benzyl or carboxymethyl.

13. A composition as claimed in claim 11, wherein said compound is selected from compounds in which $R^2$ represents a hydrogen atom and salts and esters thereof.

14. A composition as claimed in claim 12 or claim 13, wherein $R^1$ represents an ethyl or isopropyl group.

15. A composition as claimed in claim 11, wherein said compound is selected from compounds of formula (IIa):

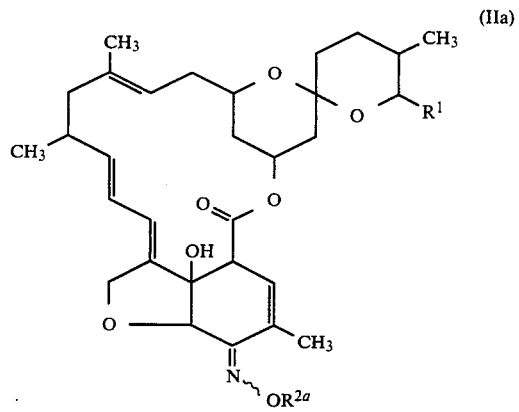

wherein:
$R^1$ represents methyl, ethyl or isopropyl; and
$R^{2a}$ represents:
a group of formula —$COR^4$, in which $R^4$ represents a $C_1$–$C_6$ alkyl group, benzyl, benzyl substituted with one $C_1$–$C_6$ alkyl, halogen or nitro, phenyl, phenyl substituted with at least one $C_1$–$C_6$ alkyl, halogen, nitro, carboxy or $C_2$–$C_7$ alkoxycarbonyl substituents or a group of formula —$(CH_2)_n COOR^5$, wherein n is an integer from 1 to 3 and $R^5$ represents a hydrogen atom or a $C_1$–$C_6$ alkyl group;

a group of formula —CO.NR⁶R⁷, wherein R⁶ represents hydrogen or a $C_1$–$C_6$ alkyl group and R⁷ represents hydrogen, a $C_1$–$C_6$ alkyl group, a phenyl group or a group of formula —CH(R⁸).COOR⁹ (wherein R⁸ and R⁹ are the same or different and each represents hydrogen or a $C_1$–$C_6$ alkyl group);

a group of formula —COR¹⁰, wherein R¹⁰ represents a $C_1$–$C_6$ alkyl group, benzyl, benzyl substituted with one $C_1$–$C_6$ alkyl, halogen or nitro, a phenyl group or a sugar alcohol from which an omega-hydroxy group has been removed, said sugar alcohol is selected from the group consisting of glycerol, erythritol, threitol, arabinitol, adonitol, xylitol, sorbitol, mannitol and dulcitol; said sugar alcohol may be substituted wih at least one protecting group selected from the group consisting of formyl, acetyl, tetrahydro-2-furanyl, tetrahydro-2-pyranyl groups, 1-methoxyethyl, 1-ethoxyethyl, trimethylsilyl, triethylsilyl and dimethyl-t-butylsilyl, and the paired hydroxy groups at the 1- and 2-positions or at the 1- and 3-positions may be joined by replacing the terminal hydrogens of respective paired hydroxy groups with a bridging methylene, ethylene, isopropylidene, benzylidene or cyclohexyline group;

a group of formula —SO₂R¹¹, wherein R¹¹ represents a $C_1$–$C_6$ alkyl group or a phenyl group; or a group of formula —(Y¹=)P(—Y²—R¹²)₂, in which Y¹ and Y², which may be the same or different, each represents oxygen or sulphur and the two atoms represented by Y² may be the same or different, and each of the groups represented by R¹², which may be the same or different, is a $C_1$–$C_6$ alkyl group.

16. A composition as claimed in claim 15, wherein R²ᵃ represents a $C_2$–$C_7$ alkanoyl group, a $C_2$–$C_7$ alkylcarbamoyl group, a ($C_1$–$C_6$ alkoxy)carbonylmethylcarbamoyl group, a $C_2$–$C_7$ alkoxycarbonyl group, a 2,2-dimethyl-1,3-dioxolan-4-ylmethoxycarbonyl group, a $C_1$–$C_6$ alkanesulphonyl group, a benzenesulphonyl group, a di($C_1$–$C_6$ alkoxy)phosphinyl group or a ($C_1$–$C_6$ alkoxy)-($C_1$–$C_6$ alkylthio)phosphinyl group.

17. A composition as claimed in claim 15, wherein R²ᵃ represents a $C_2$–$C_7$ alkanoyl group, a $C_2$–$C_7$ alkylcarbamoyl group, a $C_2$–$C_7$ alkoxycarbonyl group or a 2,2-dimethyl-1,3-dioxolan-4-ylmethoxycarbonyl group.

18. A composition as claimed in claim 16 or claim 17, wherein R¹ represents an ethyl or isopropyl group.

19. A composition as claimed in any one of claims 11, 12 and 13, wherein said compound is selected from sodium and potassium salts.

20. A composition as claimed in claim 19, wherein R¹ represents ethyl or isopropyl.

21. A method of treating an animal parasitized by a parasite selected from helminths, acarids and insects, which comprises applying to or administering to said animal an effective amount of an active compound, wherein said active compound is selected from a compound of formula (II):

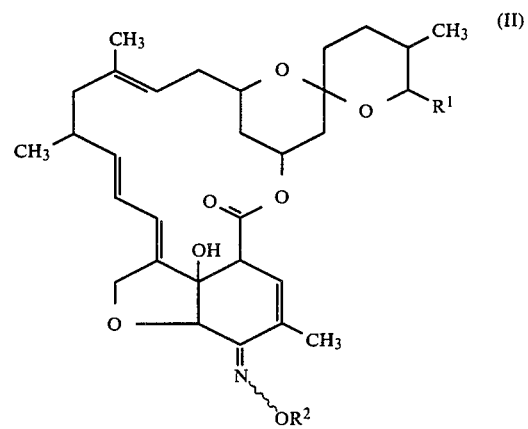

in which R¹ represents methyl, ethyl or isopropyl and R² represents hydrogen, a $C_1$–$C_6$ alkyl group, benzyl, benzyl substituted with one $C_1$–$C_6$ alkyl, halogen or nitro or a group of formula —CH₂COOR³, in which R³ represents hydrogen or a $C_1$–$C_6$ alkyl group; and, when R² represents hydrogen, a veterinary or an agriculturally acceptable salt or ester thereof.

22. The method as claimed in claim 21, wherein R² represents hydrogen, a $C_1$–$C_6$ alkyl group, benzyl or carboxymethyl.

23. The method as claimed in claim 21, wherein said compound is selected from compounds in which R² represents a hydrogen atom and salts and esters thereof.

24. The method as claimed in claim 22 or claim 23, wherein R¹ represents an ethyl or isopropyl group.

25. A method as claimed in claim 21, wherein said compound is selected from compounds of formula (IIa):

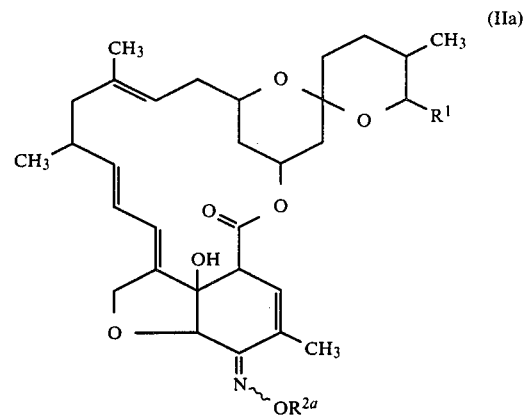

wherein:
R¹ represents methyl, ethyl or isopropyl; and
R²ᵃ represents:
a group of formula —COR⁴, in which R⁴ represents a $C_1$–$C_6$ alkyl group, benzyl, benzyl substituted with one $C_1$–$C_6$ alkyl, halogen or nitro, phenyl, phenyl substituted with at least one $C_1$–$C_6$ alkyl, halogen, nitro, carboxy or $C_2$–$C_7$ alkoxycarbonyl substituents or a group of formula —(CH₂)ₙCOOR⁵, wherein n is an integer from 1 to 3 and R⁵ represnts a hydrogen atom or a $C_1$–$C_6$ alkyl group;

a group of formula —CO.NR⁶R⁷, wherein R⁶ represents hydrogen or a $C_1$–$C_6$ alkyl group and R⁷ represents hydrogen, a $C_1$-$C_6$ alkyl group, a phenyl group or a group of formula —CH($R^8$).COO$R^9$ (wherein $R^8$ and $R^9$ are the same or different and each represents hydrogen or a $C_1$-$C_6$ alkyl group);

a group of formula —COO$R^{10}$, wherein $R^{10}$ represents a $C_1$-$C_6$ alkyl group, benzyl, benzyl substituted with one $C_1$-$C_6$ alkyl, halogen or nitro, a phenyl group or a sugar alcohol from which an omega-hydroxy group has been removed, said sugar alcohol is selected from the group consisting of glycerol, erythritol, threitol, arabinitol, adonitol, xylitol, sorbitol, mannitol and dulcitol; said sugar alcohol may be substituted with at least one protecting group selected from the group consisting of formyl, acetyl, tetrahydro-2-furanyl, tetrahydro-2-pyranyl groups, 1-methoxyethyl, 1-ethoxyethyl, trimethylsilyl, triethylsilyl and dimethyl-t-butylsilyl, and the paired hydroxy groups at the 1- and 2-positions or at the 1- and 3-positions may be joined by replacing the terminal hydrogens of respective paired hydroxy groups with a bridging methylene, ethylene, isopropylidene, benzylidene or cyclohexyline group;

a group of formula —SO$_2$$R^{11}$, wherein $R^{11}$ represents a $C_1$-$C_6$ alkyl group or a phenyl group; or a group of formula —($Y^1$=)P(—$Y^2$—$R^{12}$)$_2$, in which $Y^1$ and $Y^2$, which may be the same or different, each represents oxygen or sulphur and the two atoms represented by $Y^2$ may be the same or different, and each of the groups represented by $R^{12}$, which may be the same or different, is a $C_1$-$C_6$ alkyl group.

26. The method as claimed in claim 25, wherein $R^{2a}$ represents a $C_2$-$C_7$ alkanoyl group, a $C_2$-$C_7$ alkylcarbamoyl group, a ($C_1$-$C_6$ alkoxy)carbonylmethylcarbamoyl group, a $C_2$-$C_7$ alkoxycarbonyl group, a 2,2-dimethyl-1,3-dioxolan-4-ylmethoxycarbonyl group, a $C_1$-$C_6$ alkanesulphonyl group, a benzenesulphonyl group, a di($C_1$-$C_6$ alkoxy)phosphinyl group or a ($C_1$-$C_6$ alkoxy)-($C_1$-$C_6$ alkylthio)phosphinyl group.

27. The method as claimed in claim 25, wherein $R^{2a}$ represents a $C_2$-$C_7$ alkanoyl group, a $C_2$-$C_7$ alkylcarbamoyl group, a $C_2$-$C_7$ alkoxycarbonyl group or a 2,2-dimethyl-1,3-dioxolan-4-ylmethoxycarbonyl group.

28. The method as claimed in claim 26 or claim 27, wherein $R^1$ represents an ethyl or isopropyl group.

29. The method as claimed in any one of claims 21, 22 and 23, wherein said compound is selected from sodium and potassium salts.

30. The method as claimed in claim 29, wherein $R^1$ represents ethyl or isopropyl.

31. A method of protecting animals or plants from damage by parasites selected from helminths, acarids and insects, which comprises applying an effective amount of an active compound to said animals, said plants or seeds of said plants or to a locus including the same, wherein said active compound is selected from a compound of formula (II):

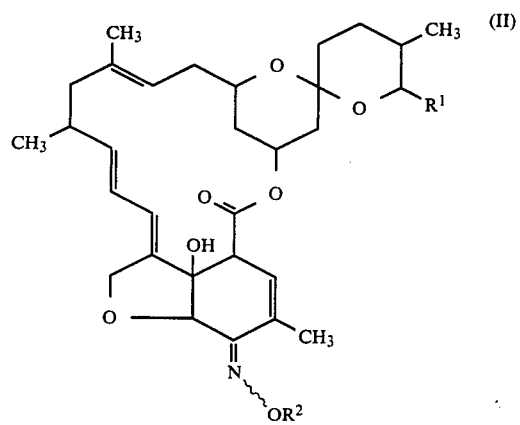

in which $R^1$ represents methyl, ethyl or isopropyl and $R^2$ represents hydrogen, a $C_1$-$C_6$ alkyl group, benzyl, benzyl substituted with one $C_1$-$C_6$ alkyl, halogen or nitro or a group of formula —CH$_2$COO$R^3$, in which $R^3$ represents hydrogen or a $C_1$-$C_6$ alkyl group; and, when $R^2$ represents hydrogen, a veterinary or an agriculturally acceptable salt or ester thereof.

32. The method as claimed in claim 31, wherein $R^2$ represents hydrogen, a $C_1$-$C_6$ alkyl group, benzyl or carboxymethyl.

33. The method as claimed in claim 31, wherein said compound is selected from compounds in which $R^2$ represents a hydrogen atom and salts and esters thereof.

34. A method as claimed in claim 32 or claim 33, wherein $R^1$ represents an ethyl or isopropyl group.

35. A method as claimed in claim 31, wherein said compound is selected from compounds of formula (IIa):

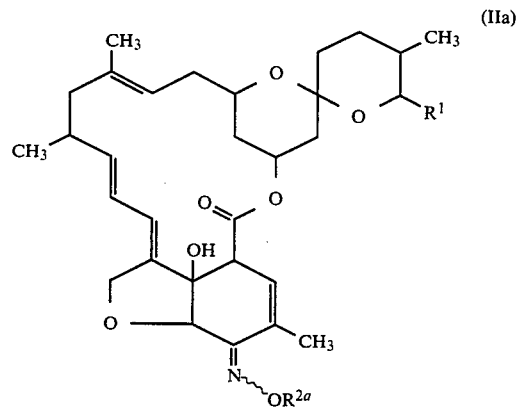

wherein:
$R^1$ represents methyl, ethyl or isopropyl; and
$R^{2a}$ represents:
a group of formula —CO$R^4$, in which $R^4$ represents a $C_1$-$C_6$ alkyl group, benzyl, benzyl substituted with one $C_1$-$C_6$ alkyl, halogen or nitro, phenyl, phenyl substituted with at least one $C_1$-$C_6$ alkyl, halogen, nitro, carboxy or $C_2$-$C_7$ alkoxycarbonyl substituents or a group of formula —(CH$_2$)$_n$COO$R^5$, wherein n is an integer from 1 to 3 and $R^5$ represnts a hydrogen atom or a $C_1$-$C_6$ alkyl group;
a group of formula —CO.N$R^6$$R^7$, wherein $R^6$ represents hydrogen or a $C_1$-$C_6$ alkyl group and $R^7$ represents hydrogen, a $C_1$-$C_6$ alkyl group, a phenyl group or a group of formula —CH($R^8$).COO$R^9$ (wherein $R^8$ and $R^9$ are the same or different and each represents hydrogen or a $C_1$-$C_6$ alkyl group); a group of formula —COO$R^{10}$, wherein $R^{10}$ represents a $C_1$-$C_6$ alkyl group, benzyl, benzyl substituted with one $C_1$-$C_6$ alkyl, halogen or nitro, a phenyl group or a sugar alcohol from which an omega-hydroxy group has been removed, said sugar alcohol is selected from the group consisting of glycerol, erythritol, threitol, arabinitol, adonitol, xylitol, sorbitol, mannitol and dulcitol; said sugar alcohol may be substituted with at least one protecting group selected from the group consisting of formyl, acetyl, tetrahydro-2-furanyl, tetrahydro-2-pyranyl groups, 1-methoxyethyl, 1-ethoxyethyl, trimethylsilyl, triethylsilyl and dimethyl-t-butylsilyl, and the paired hydroxy groups at the 1- and 2-positions or at the 1- and 3-positions may be joined by replacing the terminal hydrogens of respective paired hydroxy groups with a bridging methylene, ethylene, isopropylidene, benzylidene or cyclohexyline group;

a group of formula —SO$_2R^{11}$, wherein $R^{11}$ represents a $C_1$-$C_6$ alkyl group or a phenyl group; or a group of formula —($Y^1$=)P(—$Y^2$—$R^{12}$)$_2$, in which $Y^1$ and $Y^2$, which may be the same or different, each represents oxygen or sulphur and the two atoms represented by $Y^2$ may be the same or different, and each of the groups represented by $R^{12}$, which may be the same or different, is a $C_1$-$C_6$ alkyl group.

36. The method as claimed in claim 35, wherein $R^{2a}$ represents a $C_2$-$C_7$ alkanoyl group, a $C_2$-$C_7$ alkylcarbamoyl group, a ($C_1$-$C_6$ alkoxy)carbonylmethylcarbamoyl group, a $C_2$-$C_7$ alkoxycarbonyl group, a 2,2-dimethyl-1,3-dioxolan-4-ylmethoxycarbonyl group, a $C_1$-$C_6$ alkanesulphonyl group, a benzenesulphonyl group, a di($C_1$-$C_6$ alkoxy)phosphinyl group or a ($C_1$-$C_6$ alkoxy)-($C_1$-$C_6$ alkylthio)phosphinyl group.

37. The method as claimed in claim 35, wherein $R^{2a}$ represents a $C_2$-$C_7$ alkanoyl group, a $C_2$-$C_7$ alkylcarbamoyl group, a $C_2$-$C_7$ alkoxycarbonyl group or a 2,2-dimethyl-1,3-dioxolan-4-ylmethoxycarbonyl group.

38. The method as claimed in claim 36 or claim 37, wherein $R^1$ represents an ethyl or isopropyl group.

39. The method as claimed in any one of claims 31, 32 and 33, wherein said compound is selected from sodium and potassium salts.

40. A method as claimed in claim 39, wherein $R^1$ represents ethyl or isopropyl.

* * * * *

UNITED STATES PATENT AND TRADEMARK OFFICE

CERTIFICATE EXTENDING PATENT TERM
UNDER 35 U.S.C. 156

Patent No.     : 4,547,520

Dated          : October 15, 1985

Inventor(s)    : Junya Ide et al.

Patent Owner   : Sankyo Co., Ltd.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

608 DAYS with all rights pertaining thereto as provided by
35 U.S.C. 156 (b).

I have caused the seal of the Patent
and Trademark Office to be affixed
this 25th day of July, 1991.

Harry F. Manbeck, Jr.
Assistant Secretary and Commissioner
   of Patents and Trademarks